United States Patent [19]

Shanbrom

[11] Patent Number: 5,609,864
[45] Date of Patent: Mar. 11, 1997

[54] PRESERVATION OF BLOOD, TISSUES AND BIOLOGICAL FLUIDS

[76] Inventor: Edward Shanbrom, 2252 Liane La., Santa Ana, Calif. 92705

[21] Appl. No.: 255,381

[22] Filed: Jun. 8, 1994

Related U.S. Application Data

[60] Division of Ser. No. 846,129, Mar. 3, 1992, Pat. No. 5,360,605, which is a continuation-in-part of Ser. No. 577,204, Sep. 4, 1990, abandoned, and a continuation-in-part of Ser. No. 577,295, Sep. 4, 1990, abandoned, and a continuation-in-part of Ser. No. 753,734, Sep. 3, 1991, abandoned, and a continuation-in-part of Ser. No. 753,814, Sep. 3, 1991, abandoned, and a continuation-in-part of Ser. No. 754,752, Sep. 4, 1991, abandoned.

[51] Int. Cl.$^6$ ............................. A61K 31/74; B01D 35/00
[52] U.S. Cl. ...................... 424/78.08; 424/667; 424/672; 210/232
[58] Field of Search ................... 424/78.08, 667, 424/672

[56] References Cited

U.S. PATENT DOCUMENTS 5,071,548  12/1991  Miller et al. .............................. 210/232

*Primary Examiner*—Zohreh Fay
*Attorney, Agent, or Firm*—Price, Gess & Ubell

[57] ABSTRACT

The treatment and preservation of blood, blood derivatives and other body tissues, fluids and cells with povidone-iodine and then quenching the oxidizing potential of iodine in the povidone iodine to kill pathogenic microbes without destroying the utility of the tissues, fluids and cells is disclosed.

7 Claims, 1 Drawing Sheet

PRESERVATION OF BLOOD, TISSUES AND BIOLOGICAL FLUIDS

CROSS-REFERENCE TO RELATED PATENT APPLICATIONS

This is a divisional of application Ser. No. 07/846,129 filed on Mar. 3, 1992, now U.S. Pat. No. 5,360,605, which is a continuation-in-part of Ser. No. 577,204, and Ser. No. 577,295, both Filed Sep. 4, 1990, both now abandoned, and Ser. No. 753,734, filed Sep. 3, 1991, now abandoned; Ser. No. 753,814, filed Sep. 3, 1991, now abandoned; and Ser. No. 754,752, filed Sep. 4, 1991, now abandoned, to which priority is claimed.

FIELD OF THE INVENTION

This invention relates to the treatment and preservation of blood and blood derivatives, the treatment and preparation of other body tissues and cells, the treatment and preparation of tissue cultures and tissue culture products, and the preparation of laboratory reagents, standards and samples. In specific and important embodiments, the invention is defined in terms of methods for treating biological materials with povidone-iodine compounds having a very high (15:1 or higher) ratio of povidone to iodine and thereafter introducing a physiologically compatible reducing agent such as an ascorbate salt and/or passing a liquid material through a bed or filter of solid, e.g. cross-linked, povidone iodine to remove the last traces of oxidizing iodine. This invention may, thus, be used to kill or inactivate virus, bacteria, chlamydia, rickettsia, mycoplasma and other potentially pathogenic microorganisms and to remove all oxidizing iodine.

The treatment and preparation of human blood, tissues, etc. and of the blood, tissues, etc. of other animals are contemplated. In general, the field of this invention lies in medicine and veterinary practice; most examples being related to the practice of medicine for the benefit of human patients, use in analogous fields of veterinary medicine to the extent applicable being within the scope of the invention.

BACKGROUND OF THE INVENTION

Iodine was officially recognized by the Pharmacopeia of the United States in 1930, also as tincture iodine (tincture of iodine) and linimentum iodi (liniment of iodine). Clinicians and microbiologists described a great number of experimental data and clinical applications. Despite the successes that have been achieved with iodine, it was ascertained early that it also possesses properties unsuitable for practical application, including, for example, the fact that iodine has an unpleasant odor. In addition, it stains the skin with an intensive yellow-brownish color, causes blue stains in the laundry in the presence of starch, and combines with iron and other metals, its solutions are not stable, it irritates animal tissue, and is a poison. The adverse side effects of iodine, its painfulness on open wounds and the possibility of allergic reactions in the past 100 years led to the production of a great many iodine compounds (and iodine preparations), with the aim of avoiding these incompatibilities without a significant loss of germicidal efficiency. In this connection, the iodophors finally succeeded as nearly ideal forms for application of iodine.

Although exact details about the killing of a living cell by the $I_2$ molecule (or one of the reaction products occurring in aqueous solution) are not known, it can be assumed that iodine reacts:

(1) With basic N—H functions that are parts of some amino acids (e.g., lysine, histidine, arginine) and the bases of nucleotides (adenine, cytosine, and guanine) forming the corresponding N-iododerivatives. By this reaction, important positions for hydrogen bonding are blocked, and a lethal disorder of the protein structure may occur.

(2) Oxidizing the S—H group of the amino acid cysteine, through which the connections of protein chains by disulfide (—S—S—) bridges, as an important factor in the synthesis of proteins, are lost.

(3) With the phenolic group of the amino acid tyrosine, forming mono- or diiodo-derivatives. In this case, the bulk of the iodine atom(s) in the ortho position may cause a form of steric hindrance in the hydrogen bonding of the phenolic OH group.

(4) With the carbon-carbon double bond (C=C) of the unsaturated fatty acids. This could lead to a change in the physical properties of the lipids and membrane immobilization.

Iodine—polymer complexes, e.g., with poly(vinyipyrrolidone) (PVP), and complexes of iodine with nonionic surfactants, eg, polyethylene glycol mono(nonylphenyl) ether have been used with considerable success. However, use in direct contact with labile biological materials has been limited because either the killing power of iodine is dissipated in the biological material or damages the biological material.

Povidone iodine is capable, in certain circumstances, of killing all classes of pathogens encountered in nosocomial infections: gram-positive and gram-negative bacteria, mycobacteria, fungi, yeasts, viruses and protozoa. Most bacteria are killed within 15 to 30 seconds of contact.

Iodine is consumed by proteinaceous substrates and its efficacy as a disinfectant is reduced at certain antiseptic applications. This is due to a reducing effect of the material to be disinfected which leads to the conversion of iodine into non-bactericidal iodide. Thus, not only the reservoir of available iodine is diminished but also the equilibrium of triiodide is influenced as well. Both of these effects cause a decrease in the proportion of free molecular iodine, the actual anti-microbial agent. When povidone-iodine preparations are contaminated with liquid substrata, e.g. blood, etc., there is, in addition, the dilution effect characteristic of povidone-iodine systems which causes an increase in the equilibrium concentration of free molecular iodine. To what extent the latter effect compensates for the other two effects depends on the content of reducing substances. Thus with full blood, a strong decrease of the concentration of free molecular iodine occurs, while, in the presence of plasma, it remains practically unchanged. Durmaz, et al, *Mikrobiyol. Bul.* 22 (3), 1988 (abstract); Gottardi W, *Hyg. Med.* 12 (4). 1987. 150–154. Nutrient broth and plasma had little inactivating activity but 1 g hemoglobin inactivated 50 mg of free I; experiments with $^{125}I$ showed that uptake of I by [human] red cells occurred rapidly. Optimal antimicrobial effects in clinical use should be achieved in relatively blood-free situations. Povidone iodine produced a potent and sometimes persistent bactericidal effect towards bacteria on healthy skin. Lacey, R. W., *J Appl Bacteriol* 46 (3). 1979. 443–450. The bactericidal activity of dilute povidone-iodine solutions is inversely proportional to the concentration of the povidone-iodine solutions and is inhibited to the greatest extent by blood, followed by pus, fat and glove powder. Zamora J L; *Surgery (St Louis)* 98 (1). 1985. 25–29; Zamora, *Am. J. Surgery,* 151, p. 400 (1986); see also, Waheed Sheikh, *Current Therapeutic Research* 40, No. 6, 1096 (1986). Van Den Broek, et al, *Antimicrobial Agents and Chemotherapy,* 1982, 593–597, suggests that povidone-iodine is bound to cell wall proteins leaving little for interaction with microorganisms in the liquid phase (See, also, Abdullah, et al., *Arzneim.Forsch./Drug Res.* 31 (I), Nr. 5, 828). Ninneman et al, *J. of Immunol.* 81, 1265 (1981) reported that povidone-iodine was absorbed in serum albumin and it is know that povidone-iodine is bound to albumin.

Iodine is used widely in human medicine is the disinfection of skin, (e.g., the preoperative preparations of the skin, the surgical disinfection of hands, the disinfection of the perineum prior to delivery, and the disinfection of the skin prior to infections and transfusions). Iodine preparations are also used for therapeutic purposes, e.g., the treatment of infected and burned skin but is a strong irritant. Iodophors largely overcome the irritation. Iodine has also been used for the disinfection of medical equipment, such as catgut, catheters, knife blades, ampules, plastic items, rubber goods, brushes, multiple-dose vials, and thermometers. The use of iodine as an aerial disinfectant has been advocated since 1926, and experiments on the disinfection of air have been carried out, mainly during World War II. Aerial disinfection of air-raid shelters with iodine vapors as a prophylactic measure against influenza has been recommended and a "relatively tolerable" concentration of 0.1 $mg/ft^3$ (3.5 $mg/m^3$) was found to be sufficient for a rapid kill of freshly sprayed salivary organisms. Obviously, one is aware of the danger that iodine vapors pose to the respiratory organs, documented by the fact that the maximum allowed concentration of iodine comes to 1.0 $mg/m^3$.

The use of "oxidizing iodine" including "compounds incorporating molecules of oxidizing iodine" e.g. absorbed or grafted on a purified vegetable carbon, as blood-contacting reagents having bactericidal and bacteriostatic action are mentioned in passing in connection with an autotransfuser device in U.S. Pat. No. 4,898,572, Surugue nee Lasnier, et al but without any explanation or elucidation.

Iodine is, thus, an excellent, prompt, effective microbicide with a broad range of action that includes almost all of the important health-related microorganisms, such as enteric bacteria, enteric viruses, bacterial viruses, and protozoan cysts, if the sometimes severe limitations inherent in its use are overcome. Mycobacteria and the spores of bacilli and clostridia can also be killed by iodine. Furthermore, iodine also exhibits a fungicidal and trichomonacidal activity. As to be expected, varying amounts of iodine are necessary to achieve complete disinfection of the different classes or organisms. Within the same class, however, the published data on the disinfecting effect of iodine correspond only to a small extent. In particular, the published killing time of spores and viruses are widely disparate.

Various authors have tried to summarize the disinfecting properties of iodine and the other halogens by reviewing the literature and analyzing the existing data. The most important conclusions are:

(1) A standard destruction (i.e., a 99.999% kill in 10 minutes at 25° C.) of enteric bacteria, amoebic cysts, and enteric viruses requires $I_2$ residuals of 0.2, 3.5, and 14.6 ppm, respectively.

(2) On a weight basis, iodine can inactivate viruses more completely over a wide range of water quality than other halogens.

(3) In the presence of organic and inorganic nitrogenous substances, iodine is the cysticide of choice because it does not produce side reactions that interfere with its disinfecting properties.

(4) Iodine would require the smallest mg/L dosage compared to chlorine or bromine to "break any water" to provide a free residual.

(5) $I_2$ is 2 to 3 times as cysticidal and 6 times as sporicidal as HOI, while HOI is at least 40 times as virucidal as $I_2$. This behavior is explained on the one hand by the higher diffusibility of molecular iodine through the cell walls of cysts and spores and on the other hand by the higher oxidizing power of HOI.

Gottardi, W. *Iodine and Iodine Compounds* in DISINFECTION, STERILIZATION, AND PRESERVATION, Third Edition, Block, Seymour S., Ed., Lea & Febiger, Philadelphia, 1983, and the references cited therein provide more details respecting the background discussed above.

Polyvinylpyrrolidone (PVP, Povidone) is manufactured by BASF Aktiengesellschaft, Unternehemensbereich Feincheme, D-6700 Ludwigshaven, Germany and sold under the trademark KOLIDON®. Povidone-iodine products and the preparation of such products are described in U.S. Pat. Nos. 2,707,701, 2,826,532, and 2,900,305 to Hosmer and Siggia, assigned to GAF Corporation and in a number of GAF Corporation publications; see, e.g. *Tableting with Povidone¾ povidone USP* (1981) and *PVP Polyvinylpyrrolidone* (1982).

There is extensive patent literature on the manufacture and use of various iodine-polymer complexes, exemplary of which are: U.S. Pat. No. 3,294,765, Hort, et al, 1966—manufacture of povidone-iodine complex; U.S. Pat. No. 3,468,831, Barabas, et. al., 1969—graft co-polymers of N-vinyl pyrrolidone; U.S. Pat. No. 3,468,832, Barabas, et.al., 1969—graft copolymers of N-vinyl pyrrolidone; U.S. Pat. No. 3,488,312, Barabas, et. al, 1970—water-insoluble graft polymer-iodine complexes; U.S. Pat. No. 3,689,438, Field, et. al., 1972—cross-linked polymer-iodine manufacture; U.S. Pat. No. 3,907,720, Field, et. al., 1975—cross-linked polymer-iodine manufacture; U.S. Pat. No. 4,017,407, Cantor, et. al., 1977—solid N-vinyl-2-pyrrolidone polymer carriers for iodine; U.S. Pat. No. 4,128,633, Lorenz et al, 1978—preparation of PVP-I complex; U.S. Pat. No. 4,139,688, Dixon, 1979—cross-linked vinyipyrrolidone; U.S. Pat. No. 4,180,633, Dixon, 1979—cross-linked vinylpyrrolidone; U.S. Pat. No. 4,190,718, Lorenz, et.al., 1980—increasing molecular weight of polyvinylpyrrolidone.

Under ordinary conditions, PVP is stable as a solid and in solution. The single most attractive property of PVP is its binding capability. This property has permitted utilization in numerous commercial applications. Small quantities of PVP stabilize aqueous emulsions and suspensions, apparently by its absorption as a thin layer on the surface of individual colloidal particles. The single most widely studied and best characterized PVP complex is that of PVP-iodine. For example, hydrogen triiodide forms a complex with PVP that is so stable that there is no appreciable vapor pressure. It is superior to tincture of iodine as a germicide.

Various poloxamers (i.e., polyether alcohols) also make effective carriers for iodine (i.e., Prepodyne, Septodyne) that exhibit the same germicidal activity as povidone-iodine. The iodophors are available in a variety of forms, such as a 10% applicator solution, 2% cleansing solution (scrub), aerosol spray, aerosol foam, vaginal gel (for trichonomal and candidal infections) ointment powder, mouthwash, perineal wash, and whirlpool concentrate (all 2%). All iodophors may be used in this invention in some of its various uses and applications and, to the extent that the iodophor is effective and does not injure the material undergoing treatment, are considered generally as equivalents or potential equivalents of povidone iodine.

As used here, the term "blood" means whole blood and blood fractions, components, and products of blood, unless "whole blood" or a specific blood derivative, e.g. a blood fraction, component or product of blood is stated. Thus, the term "blood" may apply to whole blood at the time of collection or a blood derivative at any stage in processing, as indicated by context. Blood derivatives mean blood components such as blood cell concentrates (red blood cells, platelets, etc.), plasma, and serum and products and factors prepared from blood such as albumin and the blood factors. Body tissues and cells means any tissue(s), organ(s) or cells or fluids which contain tissue(s), organ(s) or cells of animal origin. Thus, in a broad sense, body tissues and cells include blood and the cellular components of blood; however, for the most part, simply for clarity in presentation, blood is treated as a separate application of the invention. Examples of body tissues and cells include sperm, bone marrow, kidneys, cornea, heart valves, tendons, ligaments, skin, homograft or xenograft implants and prosthesis generally. Tissue and cell cultures means cells and tissues grown or enhanced in culture media and the culture media per so, but not including nutrients intended for use in cell cultures. Examples of a cultured tissue is cultured skin tissue for use in burn victims, cells and cellular products prepared by standard biological and/or genetic engineering techniques are other examples of tissue cultures. Laboratory reagents and standards, as used in this specification and the claims, means reagents and standards produced from or comprising human or animal fluids, cells or tissues. Examples of such products are red blood cell panel utilized for typing blood, control sera and chemistry controls. Samples of tissues and fluids to be tested include samples of blood, urine, sputum, cell smears, etc. While the term "donor" is not usually applied to the individual from whom such samples are acquired, that term, "donor" will be used here in a more general sense to include the individual from whom any blood, tissue, cells or fluid is obtained for any purpose, and such term will be used to refer even to an unwilling donor.

If a tissue is explanted into the culture media for the purpose of propagating its cells, the procedure is called tissue culture whereas the explanting of individual cells into culture media would be called cell culture; however, both procedures are often referred to by the term "tissue culture" procedures without differentiation, unless the distinction is critical for some ancillary reason. This general usage of the term is employed here.

Tissue cultured cells are extremely fragile in many ways, having exacting requirements not only as to nutrients but also to the amount and type of resident organisms which can be tolerated, and culture media are highly susceptible to bacterial and/or viral infection.

Povidone is used generally to describe compounds described in the U.S. Pharmacopeia to identify polyvinyl pyrrolidone suitable for use in physiologically acceptable solutions and to include polyvinylpyrrolidone (PVP) compositions that have not yet been approved for use in the preparation of therapeutic compounds, and equivalents, as described hereinbefore. When percent concentrations are referred to in connection with povidone-iodine, the percentage refers to the percent of povidone-iodine by weight, based upon the weight of the solution or material to which the povidone-iodine is added. Thus, a 1 weight percent (w/o) solution of povidone-iodine indicates that enough povidone-iodine has been dissolved to result in a concentration of 1 w/o povidone-iodine. The ratio of polyvinyl pyrrolidone to iodine in the povidone-iodine product used in the experiments referred to hereinafter is 8.5 parts of povidone-iodine per 1 part of active iodine. The product also contains about 0.5 parts of inactive iodine as iodide. Typical stock solutions are 10% (10,000 ppm $I_2$), 5% (5,000 ppm $I_2$) and 1% (100 ppm $I_2$). In those instances in which a povidone to iodine ratio of higher than about 8.5 to 1 is referred to, additional povidone (polyvinyl pyrrolidone) is added to increase the PVP to $I_2$ ratio. The concentration of povidone-iodine in such compositions means the concentration of standard PVP-I (calculated as having an 8:5 to 1 PVP to $I_2$ ratio, whether or not added in that ratio. PVP in excess is treated, for purposes of calculation, separately from the PVP in "standard" povidone iodine.

PVP-I-PVP is used as an abbreviation for povidone enriched povidone iodine, i.e a composition in which the total povidone to iodine ratio is greater than 15 to 1.

PVP-I-PVPLMW is used as an abbreviation for PVP-I-PVP in which at least ten percent of the povidone has a molecular weight of no greater than approximately 12,000 daltons.

PVP-I-PVPXL is used as an abbreviation for a composition that, as to synthetic polymeric materials, consists essentially of soluble PVP-I and solid PVP, typically cross-linked PVP.

XLPVP-I is used as an abbreviation for iodinated solid, e.g. cross-linked, povidone.

Those who deal with blood and other invasively obtained body fluid samples risk infection from the samples. Those at risk include the doctor, nurse or clinical technician who takes the sample, the technicians who handle the sample and who use the sample in conducting analyses and tests, those who handle the sampling and testing equipment and apparatus, and the entire chain of individuals who attend to the disposal of sampling apparatus and the like, from the individuals who pick up the used apparatus through those who ultimately dispose of the apparatus, usually in specially designed high temperature furnaces. The risk is substantial, as evidenced by the fact that nearly all health care professionals with long experience carry the Epstein-Barr virus (EBV) and/or cytomegalovirus (CMV). Other pathogenic viruses to which health care workers, and those who handle blood and fluid sampling and handling apparatus, are exposed include hepatitis and human immunodeficiency virus (HIV) as well as a large number of less life-threatening viruses.

Another organism which is frequently present in blood and blood products or fractions and which presents a serious risk in certain procedures is the bacteria *Yersinia enterocolitica* which is become a serious contaminant, surpassing Salmonella and Campylobacter as a cause of acute bacterial gastroenteritis. A significant increase in transfusion related infections of *Y. enterocolitica* has been reported, Tipple, et al., *Transfusion* 30, 3, p.207 (1990). *Y. enterocolitica* and other bacteria which propagate at relatively low temperatures, e.g. *Staphylococcus epidermis* and *Legionella pneumophila*, present, potentially, a serious threat in blood products.

In addition to the risk of transmitting infectious disease via blood or blood products, the growth of bacteria in blood and blood products at various stages of production and processing introduces pyrogens into the blood component or product which must be removed before the product can be used in therapy. Introduction of molecular iodine, e.g. povidone-$I_2$, at an early stage in processing of blood products greatly reduces or eliminates the pyrogen-load of the ultimate product or fraction.

Protozoa give rise to many diseases, some of great medical and economic importance. Examples of such protozoa are the genus Plasmodium, e.g. *P. falciparum, P. malariae, P. ovale* and *P. vivax*, which causes malaria, Trypanosoma, which causes Chagas' disease, and Leishmania, which cause a variety of leishmaniasis. The method of this invention is effective in eliminating these causative organisms in blood and blood products.

Many viruses, in both animals and humans, may be transmitted by artificial insemination using sperm from infected individuals. Bovine leucosis (Mateva, V. et al, *Monatsh. Veterinaermed.* 1987, 42(9) 310) and bovine rhinotracheitis virus are transmitted by sperm of infected bulls. (Kupferschmied, H. U., et al *Theriogenology* 1986, 25(3) 439). Singh, E. L. ((10*th Int. Cong. on Animal Repr. and Artificial Insemination, Cong. Proc. V.I–IV*, 1984) concluded that some viruses, e.g. bluetongue virus (BTV), infectious bovine rhinotracheitis virus (IBRV), bovine viral diarrhea virus (BVDV), foot and mouth virus (FMDV), akabane virus (AV) and bovine parvovirus (BPVP), were transmitted via seminal fluid rather than in the sperm cell.

Generally, this invention is applicable to the treatment of donated blood and products produced from blood, tissues and fluids for inactivating virus, bacteria, chlamydia, rickettsia, mycoplasma and other potentially pathogenic microorganisms.

Among the important potential pathogens to which this invention is applicable is cytomegalovirus (CMV). Herpesviruses, of which CMV is a member, represent a very large group of viruses which are responsible for, or involved in, cold sores, shingles, a venereal disease, mononucleosis, eye infections, birth defects and probably several cancers. The present invention is also useful in preventing the transmission of human immunodeficieney virus (HIV). While testing has made blood products safer than it was a decade ago, the complete elimination of HIV contaminated blood and blood products has not been possible using present knowledge and technology.

Blood plasma is used in the production of many important blood fractions, components and products. Transfusion plasma, per se, is frequently prepared as a single blood bag product; however, many plasma fractions and products are produced from large pools of plasma. There is a real and serious risk of infection to the technicians who handle individual blood bags and serum bags, and the risk of infection is multiplied many times in the handling of pooled plasma. There is, of course, a serious risk that the recipient of plasma or a plasma fraction or product may be infected unless suitable steps are taken to kill or inactivate potentially pathogenic organisms. Such steps are usually taken far down the chain of processing steps and frequently as the final step before use, storage or lyophilization, according to the product.

The production of pyrogens in plasma and plasma products during initial handling or handling down-stream in the process chain by the propagation of organisms which, at a later stage in processing, are inactivated or killed constitutes a serious problem to producers of plasma fractions and products. Pyrogen production could be eliminated or substantially reduced if pyrogen producing organisms were killed early in the process, e.g. in the initial whole blood or in the pooled plasma.

Virus infections, among the most serious being hepatitis, present a constant and serious risk to both handlers and recipients of blood and blood products. It has been shown that fractionation workers, particularly those engaged in the preparation of plasma pools, are at high risk of developing hepatitis B. The high risk products are fibrinogen, AHF, and prothrombin complex. The low risk products are ISG, PPF, and albumin. The lack of infectivity of PPF and albumin is attributable to heating the final products at 60° C. for 10 hours; however, such process steps tend to denature certain products and are unsuitable in the preparation of heat sensitive products.

The risks of infection from whole blood are well-known. One of the great tragedies of modern medicine is the infection of many patients, most frequently hemophiliacs who require frequent blood transfusions, with HIV. The purification of the nation's and the world's whole blood for transfusion would constitute a monumental step forward in the history of medicine. The risks of infection from red blood cell concentrates is similar to comparable risks associated with whole blood.

The teachings of the prior art suggest that neither elemental (diatomic) iodine nor complexed iodine, e.g. PVP-$I_2$, would be an effective and reliable biocide in a fluid or in a body, e.g. blood, packed or concentrated cells, organs, etc. in which massive amounts of protein are be available to react with the iodine.

The use of povidone-iodine as a spermicide is known and one would not consider povidone-iodine as a candidate for killing pathogenic microbes in sperm-carrying liquids.

Various medical and blood handling procedures are referred to hereinafter. These are all well-known procedures and steps in these procedures are fully described in the literature. The following references are provided for general background and as sources for detailed reference to the literature as to specific procedures: TECHNICAL MANUAL of the American Association of Blood Bankers, 9th Ed. (1985); HLA TECHNIQUES FOR BLOOD BANKERS, American Association of Blood Bankers (1984); Developments in Biological Standardization, Vols. 1–57, S. Karger, Basel; CLINICAL IMMUNOCHEMISTRY, The American Association for Clinical Chemistry; MEDICINE, Vols. 1–2, Scientific American, New York; Care of the SURGICAL PATIENT, Vols 1–2, Scientific American, New York; CURRENT PROTOCOLS IN MOLECULAR BIOLOGY, Greene Publishing Associates and Wiley-Interscience, John Wiley & Sons, New York.

SUMMARY OF THE INVENTION

Removal of iodine from biological materials treated with povidone may be essential in the manufacture or use of various therapeutic materials and may be important to optimize yield and minimize destruction of labile proteins and other constituents of biological materials. In accordance with this invention, liquid, cell-containing liquid, and proteinaceous tissues are treated with physiologically acceptable reducing compounds such as ascorbic acid and its salts, reducing sugars, sodium sulfite, etc., to reduce all iodine to iodide before transplanting or transfusing the product into the body or otherwise used. One facet of this invention involves the removal of oxidizing iodine, either by reducing it to iodide or absorption. This general method, first conceived by the present inventor with respect to blood and blood products, cell cultures, proteinaceous tissues, etc., has more recently been applied to bones and bone compositions as described in U.S. patent application Ser. No. 07/815,394, filed Dec. 31, 1991, by the present inventor, Edward Shanbrom, and Brenda Smith Morse. It has been determined that 50 μl of 1M sodium ascorbate at pH 6.5 is sufficient to neutralize 10 ml of 1% povidone iodine (which contains 0.1% $I_2$. In addition, it has been discovered that povidone has been found to possess a sufficient cytophylactic effect upon blood cells, e.g., red blood cells, and upon other cells and tissues to protect cells and tissues from the cytolytic effect of iodine when the ratio of PVP to $I_2$ is sufficiently high, e.g. about 15:1, preferably at least about 20:1, (by weight) or higher. The preferred range of povidone to iodine ratios is from about 20:1 to 30:1, but ratios as high as 60:1 are considered suitable. Higher ratios may be used but are of no greater advantage. Low molecular weight povidone is particularly valuable in this invention.

Also, according to this invention, the combination of using a high povidone to iodine ratio povidone iodine and the use of reducing substances to eliminate iodine effectively kills microbes in biological materials and eliminates excess iodine. After treatment with high povidone:iodine ratio povidone iodine, preferably including low molecular weight povidone, the product may be passed through a bed of solid povidone, e.g. cross-linked povidone, and/or treated by the addition of a reducing agent to eliminate the last traces of oxidizing iodine. Reducing sugars, ascorbic acid (Vitamin C) and its salts, and sodium sulfite are well-known, readily available reducing agents that are physiologically acceptable. However, any physiologically acceptable reducing agents may be used.

DESCRIPTION OF THE PREFERRED EMBODIMENTS

In a general sense, this invention comprises the use of povidone-iodine having a povidone:iodine ratio of at least 15:1, PVP-I-PVP, and/or using a physiologically acceptable reducing agent to remove excess iodine in the manufacture of a medicament, treatment of blood and blood products, cell culture nutrient and media, proteinaceous tissues and the like.

In the manufacture of a transfusion or transplant material, or a medicament, for example, consisting essentially of blood cells in plasma or another carrier liquid, biological liquids that may or may not carry cellular constituents, proteinaceous tissues, for use in the treatment of disorders wherein the patient requires the transfusion of blood cells, in other therapeutic procedures, in cell cultures, etc., povidone, and most preferably, low molecular weight povidone, i.e. MW<15,000, is added, i.e. PVP-I-PVPLMW. Either simultaneously therewith, or afterward, povidone-iodine in an amount in excess of that required to kill or inactivate all microbes is added. Povidone-Iodine may comprise, for example, from 0.01 to 10 weight percent, preferably from about 0.1 w/o to 5 w/o of the composition. The povidone iodine is allowed to remain in contact with the blood cells or plasma, or other biological material being prepared to be a medicament, for a period of at least about a half a minute sufficient to kill the microbes, but not long enough to denature or otherwise injure the biological material. Usually, contact of under an hour is preferred. Accordingly, the contact times will be referred to as from one-half minute to one hour with the caveat that longer contact is not necessary or beneficial and may result in injury to the biological, but would, nevertheless, be within the scope of the invention. The reducing agent is then added in an amount to reduce substantially all iodine. The maximum amount of reducing agent required is easily calculated. The actual amount normally required, to which a safety margin amount will be added, is determined by an iodine assay on typical batches using known, routine procedures. A second treatment as described may be performed to assure total sterilization, if desired. Likewise, a second similar treatment may be performed on a product or fraction of the initial biological material treated as described above.

Reference is made to the "addition" of a reducing agent to the material undergoing treatment. This "addition" may be accomplished by passing the material through a layer of substantially insoluble material that has active reducing sites thereon or equilibrates with the liquid material undergoing treatment to partially dissolve into such liquid, or make readily available in said liquid (as by swelling, for example) reducing moieties. A bed of beads or fibers, for example, that expose on the surface thereof reducing sugar moieties may be used very conveniently.

Figure 1:
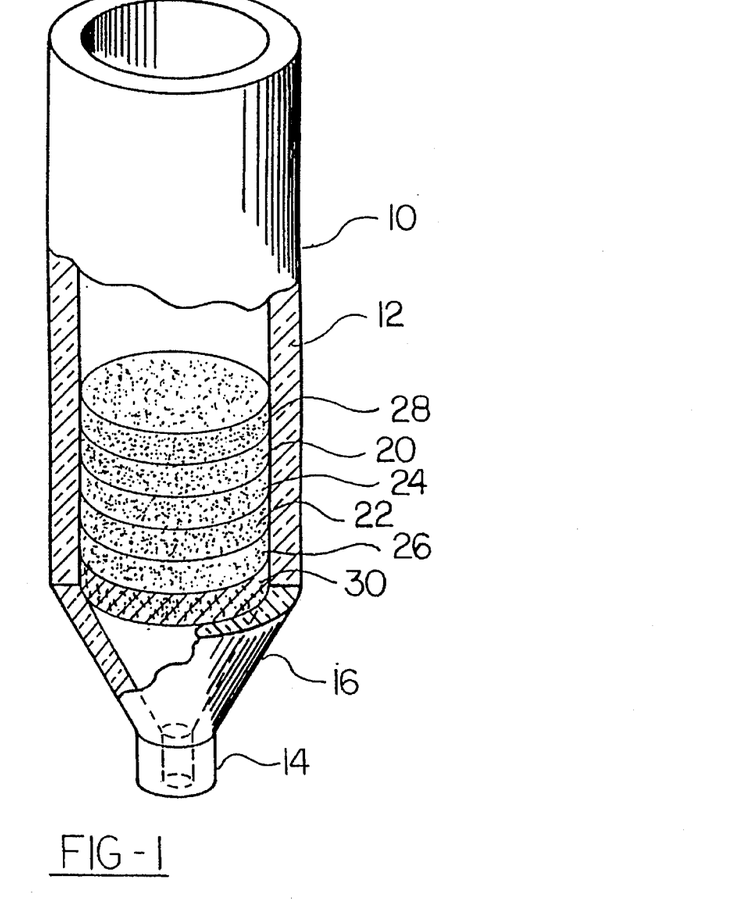
FIG. 1 depicts an apparatus for contacting a liquid material with povidone iodine and with either or both of (a) an iodine absorbing material and/or (b) an iodine reducing material, and for providing other materials for processing biological liquids, in particular, according to this invention.

Reference is made to FIG. 1 of the drawing for a better understanding of the invention in one form. FIG. 1 depicts an apparatus for contacting a liquid material with povidone iodine and with either or both of (a) an iodine absorbing material and/or (b) an iodine reducing material, and for providing other materials for processing biological liquids, in particular, according to this invention. The apparatus, being shown and described in a generally schematic fashion, may be in any of many configurations. The only significant structure, insofar as this invention relates is to the arrangement of the layers The apparatus 10 may be viewed as a filter funnel or a column. As those in the art understand, the difference between a filter and a column is often insignificant in that both "filter" a liquid and both cause the liquid to contact solid material. A filter may, indeed must, remove only part of the material. For example, either a filter or a column may let small cells or particles pass but retain larger cells, or it may permit only liquid and extremely small particles pass. The apparatus comprises cylindrical portion 12 that, in part, defines a reservoir portion. The reservoir may be large or very small as desired. The apparatus, in the configuration depicted comprises a second, smaller cylindrical tube portion 14 and a conical transition zone 16 connecting the two cylindrical portions as is conventional in funnel manufacture. It is again emphasized, however, that it is immaterial whether the apparatus defines a reservoir and or funnel portion of any particular size or configuration.

The apparatus defines a first layer 20 and a second layer 22. The first layer is made up of substantially insoluble PVP-I, e.g. XLPVP-I. This layer is described as being made up of particulate materials in that the use or particulates in one way or another is usually involved. Particles of solid, insoluble povidone-iodine, e.g. cross-linked povidone iodine, in the form of a layer or bed of particles, either supported directly by a layer below or by way of another support, e.g. being bonded to or entrapped within a layer of fibers or particles, is contemplated. The first layer may also contain some soluble PVP-I, thus comprising a bed of PVP-I-PVPXL. A frit made of particles bound together adhesively, by heat or pressure would also be within the disclosure and invention. The PVP-I may be formed in situ by iodinating a layer of PVP or the layer may be made up of pre-synthesized XLPVP-I or PVP-I-PVPXL.

The second layer is downstream of the first layer, i.e. the liquid to be treated flows through the first layer and then the second layer. The second layer may comprise an insoluble iodine absorbent, e.g. XLPVP, or an iodine reducing agent, or a mixture of both, or be a multiple sub-layer structure with a sublayer of iodine absorbent first and then a sublayer of iodine reductant. Again, the layer may be a self-supporting frit or other structure or may be supported by a support or other layer.

The essential function of the apparatus is to cause a liquid that is to be treated to pass, with or without cells or other particles therein, first through a layer of povidone iodine and, thereafter, to contact such liquid with absorbent to remove the iodine and/or reductant to reduce the iodine. Hence, the layers may be quite deep or quite thin, adjacent each other or spaced from each other, as is necessary or desirable to provide adequate contact of the liquid with each of the layers or beds.

Such an apparatus is conveniently suited for the treatment of liquid to kill microbes in the liquid. The liquid container that is generally defined by the overall apparatus in the simplified, schematic example of FIG. 1, and has an upper or liquid inflow reservoir portion for holding liquid to be treated. This may be a very small reservoir or quite large. The reservoir may displaced from the beds or layers by a very large distance, though this is not generally beneficial. The apparatus has a lower or elutriation or recovery portion for recovering liquid that has been treated. Between these portions, first and second beds of particulate matter are defined by suitable structure. The first bed or layer comprises substantially insoluble povidone iodine. The second bed consists essentially of substantially insoluble povidone, or other iodine absorbent, and/or iodine reducing agent. The beds are so formed and configured as to permit the passage of the liquid therethrough in intimate contact with the surfaces of the particles forming the respective beds. The usual and most common iodine absorbent is cross-linked povidone.

The apparatus may desirably further comprise a third layer 24 between the first and second layers. The third layer comprises substantially insoluble povidone hydrogen peroxide particulate matter. The presence of the third layer, after the povidone-iodine layer, entraps and regenerates iodine and significantly increases the biocidal activity of iodine.

A fourth layer 26, which may be in the form of a sublayer within the second layer, comprising particulate iodine reducing agent may be provided downstream from the second layer to provide for the reduction of any residual iodine from $I_2$ to iodide, or, if reduction is earlier provided, to add a safety step to assure that all oxidizing iodine has been reduced.

In may applications, it may be desirable to provide a fifth layer 28 of soluble povidone iodine on the first layer in the liquid reservoir to permit the actual dissolution into the liquid of substantial amounts of povidone iodine, preferably PVP-I-PVPLMW, and thereby provide a greater reservoir of more available iodine to the liquid.

The fifth layer may also comprise soluble povidone, preferably low molecular weight (MW<12,000 daltons) on the top of the first layer for being dissolved into the liquid to be treated to provide a cell protective milieu for the cells carried by the liquid. In like manner, the fifth layer may comprise soluble PVP-I and soluble PVP, PVP-I-PVPLMW, to provide both iodine and cell protection. Preferably, at least about one-fourth of all the PVP in solution is low molecular weight PVP, i.e., MW<$^{18}$15,000.

The first and second layers are essential to the full and proper functioning of the apparatus. After those layers or beds, however, any number of additional layers or additives may be provided, so long as they do not interfere with the combined function of the first and second beds or layers.

All of the layers just described may, conveniently but not necessarily, be supported by a layer 30 that may be a flit, a filter paper or a porous layer. The thickness of the beds may be the same or greatly different. It is a simple matter to calculate contact time in a column and to provide suitable beds of materials therein.

Any of the beds may be made up the active material, e.g. povidone iodine, reducing sugar, etc., attache to carrier particles, such as ground glass, charcoal, ion exchange resin, cellulose derivatives, etc. The particulate matter may, in a preferred form, consist essentially of particles having a diameter of from about 10 to about 100 microns, but any size that permits suitable flow rates and assures intimate contact may be used.

The use of high povidone:iodine ratio povidone-iodine and/or a physiologically acceptable reducing agent for the manufacture of transfusion biological material from one human or mammal for transfusion of such material to another human or mammal, or the transplant or transfusion biological material is a part of this invention. The transfusion or transplant is disinfected with a povidone-iodine solution having concentration of from 0.01 w/o to 10 w/o and optionally thereafter treated with the reducing agent to reduce the residual iodine. Liquid materials may be treated in any suitable manner, such as has been described. Solid tissue samples may be treated simply be soaking, by infusing or by vacuum infusing.

Figure 2:
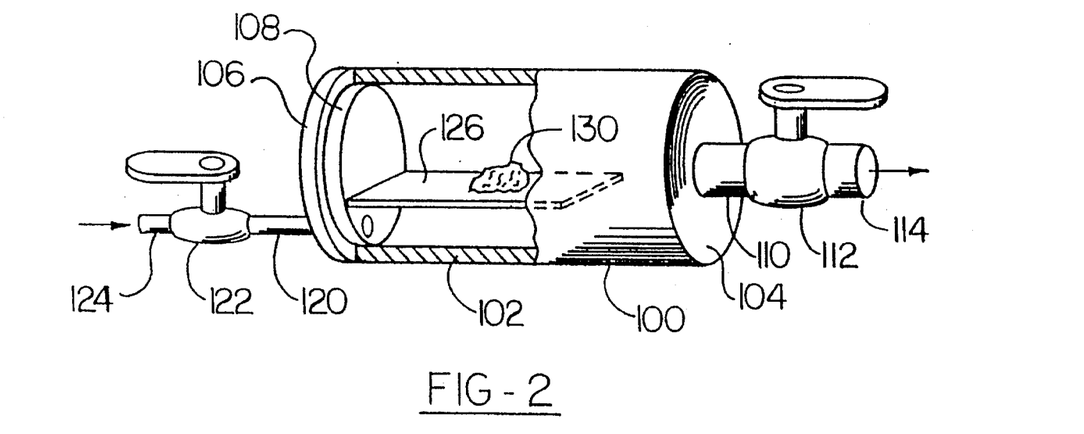
FIG. 2 depicts, largely schematically, an apparatus for treating solid tissue samples.

FIG. 2 depicts, largely schematically, an apparatus for treating solid tissue samples. The apparatus comprises a chamber system 100 capable of withstanding the forces of a vacuum. In the merely exemplary form shown, a cylinder 102 is closed at the respective ends by end covers 104 and 106, the end 106 being removable to gain access to the inside of the chamber. For example, a portion 108 of the end 106 may be slipped into the cylinder 102 and sealed using "O" rings, etc., to provide a vacuum tight seal. A vacuum line 110 through valve 112 and line 114 permits evacuation of the chamber. An input line 120, coupled to valve 122 and line 124 permits the introduction of liquid into the chamber. A platform 126, secured to the end 106, supports a tissue sample 130. The tissue sample is placed in the chamber, the chamber evacuated and then liquid is introduced, thereby substantially replacing water in the sample with the liquid introduced.

Implantable tissues may be treated to kill microbes, i.e. "sterilized" by placing tissue that is physiologically acceptable for implantation into a human patient into a vacuum chamber, evacuating the chamber and maintaining a vacuum for a period long enough to extract at least about one-half of the unbound water originally present in said tissue and then introducing into said vacuum chamber a solution of povidone iodine, preferably PVP-I-PVPLMW, for thereby reconstituting into the tissue said solution in place of the water that was vacuum extracted. The thus treated tissue may optionally then be soaked in a solution of an physiologically acceptable iodine reducing agent. Alternatively, the chamber may again be evacuated to extract the povidone iodine solution from the tissue and a solution of physiologically acceptable iodine reducing agent introduced into the vacuum chamber for saturating the tissue for reducing any residual iodine.

As a method of disinfecting blood derivatives, the invention may comprise treating blood before separation of the components thereof with povidone-iodine to provide from a concentration of from about 0.01 to 10 weight percent, preferably from about 0.1 w/o to 5 w/o povidone-iodine, e.g.

as PVP-I-PVPLMW, in the blood, preparing a derivative of the blood from step, optionally treating the derivative with povidone-iodine to provide from about 0.01 to 10 weight percent, preferably from about 0.1 w/o to 5 w/o, in the derivative and optionally thereafter treating the derivative by addition of a physiologically acceptable reducing agent or contact with cross-linked PVP to reduce or remove residual iodine.

Data tabulated in Table I shows that PVP, alone, has viricidal activity and that povidone-iodine is effective in killing virus in whole blood and in cell concentrates.

TABLE I

KILL OF VSV IN PLASMA WITH PVP AND PVP-I

| | LOG KILL IN >>> | 1 HOUR | 24 HOURS |
|---|---|---|---|
| 1 | 3% PVP C-15[1] | 1.67 | 2.0 |
| 2 | 2% PVP C-15 | 2.0 | 3.0 |
| 3 | 1% PVP C-15 | 2.33 | 3.0 |
| 4 | 3% PVP C-15 + 0.25% PVP-I[2] | 5.33 | 8+ |
| 5 | 2% PVP C-15 + 0.25% PVP-I | 5.0 | 8+ |
| 6 | 1% PVP C-15 + 0.25% PVP-I | 4.67 | 8+ |
| 7 | 3% PVP C-15 + 0.10% PVP-I | 4.33 | 5.5 |
| 8 | 2% PVP C-15 + 0.10% PVP-I | 4.33 | 6.33 |
| 9 | 1% PVP C-15 + 0.10% PVP-I | 4.33 | 5.33 |
| 10 | 3% PVP C-30[3] | 3.33 | 4.33 |
| 11 | 2% PVP C-30 | 3.0 | 4.33 |
| 12 | 1% PVP C-30 | 3.33 | 5.0 |
| 13 | 3% PVP C-30 + 0.25% PVP-I | 6.67 | 8+ |
| 14 | 2% PVP C-30 + 0.25% PVP-I | 7.33 | 8+ |
| 15 | 1% PVP C-30 + 0.25% PVP-I | 8+ | 8+ |
| 16 | 3% PVP C-30 + 0.10% PVP-I | 4.5 | 6.67 |
| 17 | 2% PVP C-30 + 0.10% PVP-I | 4.67 | 6.5 |
| 18 | 1% PVP C-30 + 0.10% PVP-I | 5.0 | 6.33 |
| 19 | 3% PVP K-26-28[4] | 3.67 | 5.67 |
| 20 | 2% PVP K-26-28 | 3.5 | 5.33 |
| 21 | 1% PVP K-26-28 | 4.0 | 5.00 |
| 22 | 3% PVP K-26-28 + 0.25% PVP-I | 8+ | 8+ |
| 23 | 2% PVP K-26-28 + 0.25% PVP-I | 8+ | 8+ |
| 24 | 1% PVP K-26-28 + 0.25% PVP-I | 8+ | 8+ |
| 25 | 3% PVP K-26-28 + 0.10% PVP-I | 5.0 | 8+ |
| 26 | 2% PVP K-26-28 + 0.10% PVP-I | 4.67 | 7.0 |
| 27 | 1% PVP K-26-28 + 0.10% PVP-I | 4.5 | 6.5 |
| 28 | 0.25% PVP-I | 4.67 | 6.0 |
| 29 | 0.10% PVP-I | 2.33 | 3.67 |
| | CONTROL | | |
| | | Virus Present | Virus Present |
| 30 | POSITIVE CONTROL (VSV/SERUM) | 8.0 LOGS | 8.0 LOGS |

[1]C-15 is polyvinyl pyrrolidone having a molecular weight of 12,500 produced by GAF Corporation.
[2]PVP-I is povidone-iodine powder produced by Purdue-Frederick Company which contains approximately 85% PVP, 10% $I_2$ and 5% Iodide.
[3]C-30 is polyvinyl pyrrolidone produced by GAF Corporation having a molecular weight of 50,000.
[4]K-26-28 is polyvinyl pyrrolidone produced by GAF Corporation having a molecular weight of between 40,000 and 50,000.

Two very important observations were made based on these and other experiments. First, increasing the povidone to iodine ratio above the ratio found in previous formulations significantly increases the biocidal effect of iodine. This result seems to be directly in conflict with what one would expect based on standard equilibrium concepts. One would expect that an increase in povidone would shift the equilibrium to reduce the amount of iodine that is free to act on microbes and other biological materials. Indeed, as discussed in detail elsewhere, this seems to be the case at least as to the protection of biological cells, e.g. red blood cells, platelets, etc. The increase in povidone to iodine ratio does indeed greatly enhance the protective characteristics of the povidone. As discussed above, the PVP-I=PVP+$I_2$ equilibrium is anomalous. Whether or not this anomaly accounts for the must unexpected increase in biocidal activity and cell protection by increasing the povidone to iodine ratio is not known. Secondly, povidone-iodine in high concentrations, e.g. higher than one percent, typically from about 1 to 5 w/o, in blood cell concentrates preserves the basic structure of the cell and generally maintains the integrity of the cell walls.

Another observation of less general application was that the povidone-iodine opens pathways through the cell wall which permits certain components of the cell, e.g. potassium salts, to "leak" from the cell. By the same mechanism, treatment of red blood cells with from one to about five percent iodine as povidone-iodine opens the cells to "inward leaking". Thus, compounds which have a virucidal or other effect in the cell can be introduced into the cell. Povidone-iodine can, for example, be used as described to increase the uptake of GTPD compounds which, in turn, prevent the replication of virus in the cell. The net effect of this procedure is a biological synergism. A new drug delivery system involves the use of povidone-iodine to open pathways through the cell wall of red blood cells. Red blood cell concentrates are treated as described to open passageways into the cell. The then permeable cell is emersed in or treated with a drug which is to be delivered to the patient. The cell walls having passages therethrough permit the drug to enter into the cell. Thereafter, the iodine may be removed and the cell concentrate is heated to 42°–48° C. to seal the cell walls. The concentrated cells are then infused into the patient where they carry out the normal function of such cells. These cells have a finite life. As the cells age, they lyse, thereby releasing the drug directly into the blood stream where the drug can become effective.

An interesting discovery was made respecting polyvinyl pyrrolidone, alone, in the course of studying the present invention. It was discovered that polyvinyl pyrrolidone alone was capable of killing about 2 to 5 logs of virus in body fluids. Whether or not there is a synergism vis-a-vis this anti-viricidal activity and the activity of iodine has not yet been determined.

Povidone-iodine is cross-linked to the hemoglobin to produce a hemoglobin product which as a greatly increased life as an oxygen carrier when introduced into the blood circulation system. Povidone-iodine-hemoglobin complex in water or saline solution, thus, constitutes a blood substitute which can be stored with minimal risk of microbial contamination and used as a blood extender in emergency situations such as may be found on the battlefield or in remote areas. Ratios of povidone-iodine to hemoglobin of from about 0.1:1.0 to about 1.0:0.1 are considered satisfactory. povidone-iodine in which the povidone:iodine ratio is at least as high as 4:1 may be preferred. The fact that povidone-iodine binds very strongly to hemoglobin allows for the development of a blood substitute. The prior art teaches the binding of PVP to hemoglobin by a variety of reagents. According to this invention, however, it has been discovered that iodine produces the binding of PVP to hemoglobin and, additionally, sterilizes the blood substitute assuring the absence of viable pathogenic organisms. Final traces of iodine may optionally be removed as described above using ascorbate, or any other suitable physiologically acceptable reducing agent, or by passing the product through a bed or layer of cross-linked PVP.

Infective pathogenic microorganisms are inactivated when molecular iodine compound is used in solution to perfuse tissues and organs after removal from the donor and before transplantation to the recipient. The perfusion solution contains molecular iodine compound in a concentration of from about 0.01 w/o to about 10 w/o (100 to 5000 ppm $I_2$), preferably from about 0.25 w/o to about 5 w/o. After a period of time, from one half minute to an hour or more, most of the unreacted molecular iodine compound is washed away and any residual molecular iodine compound is absorbed into the protein or, optionally, converted to inactive iodides, e.g. using ascorbate or other reducing agent as described, and does not significantly interfere with acceptance by the recipient.

Sperm-bearing solutions can be freed of pathogenic microbes by washing and/or storing the sperm in a solution which contains a concentration of povidone-iodine in a concentration is from about $0.0^1$ to 10 weight percent, preferably from 0.1 to about 5 w/o, (100 to 1000 ppm $I_2$) and, preferably, wherein polyvinyl pyrrolidone is added to give a polyvinyl pyrrolidone to iodine ratio is at least about 30 to about 1, the iodine concentration being sufficient to inactivate bacteria, viruses and other pathogenic organisms, and washing the sperm cells in the solution. It has been discovered that polyvinyl pyrrolidone protects the sperm cells from the spermicidal activity of iodine sufficient to permit the killing of pathogenic organisms while leaving viable, motile sperm cells suitable for artificial insemination. The washing is continued or repeated to assure that substantially all of the seminal fluid is replaced with povidone-iodine solution. Other reagents such as are conventionally used in sperm treatment, storage and preparation, or for particular purposes may, of course, also be included in the infusion solution. If desired, residual iodine may be washed out and/or removed using ascorbate or other reducing agent and any suitable storage fluid, including solutions of polyvinyl pyrrolidone, may be used to store and handle the sperm cells. The invention also contemplates a composition of matter consisting essentially of povidone and iodine wherein the ratio of povidone to iodine is from 15 to 60 parts of povidone to 1 part of iodine. Such compositions of matter may be powdered povidone-iodine with an increased amount of povidone or solutions of the same.

The above applications in which the material to be purified is a liquid or cells carried in a liquid can be carried out by flowing the liquid through a bed (e.g. the conventional filter structure of solid particles on a porous or foraminous support) of solid particles of povidone-iodine of suitable size or by contacting the liquid and/or the cells in the liquid with particles or a membrane or surface of solid povidone-iodine. Where a bed of particles is used with a cell-bearing liquid, the particles must be large enough to permit intimate contact without entrapping or binding the cells. One particularly advantageous method is to add low molecular weight PVP, MW<15,000, to the liquid to be treated, to protect the cells and provide the additional PVP necessary to achieve an ultimate PVP:I ratio of >15:1, then add soluble povidone-iodine. The liquid may then be passed through a layer or in contact with cross-linked povidone-iodine to assure complete biocidal effect. Thereafter, the liquid is passed through or into intimate contact with cross-linked PVP to absorb the molecular iodine from the liquid. Finally, a reducing agent such as ascorbate may be added if considered necessary as a precaution.

Polyvinyl pyrrolidone used in the preparation of soluble povidone-iodine preparations is polymerized to a molecular weight of from 10K daltons to 40K daltons, 30K daltons being a typical molecular weight. However, povidone-iodine preparations can be prepared using very much higher molecular weight polymers which only tend to swell rather than to dissolve in aqueous solutions. It is the use of these higher molecular weight polyvinyl pyrrolidone polymers reacted with iodine, which causes cross-linking, to form solid, substantially water insoluble povidone-iodine compositions that the present invention is directed.

In carrying out this facet of the invention, the liquid or cell-bearing liquid is contacted with the solid povidone-iodine. This may be done most efficiently, in most cases, by passing the liquid through a settled or fluidized or packed bed of povidone-iodine particles; however, such approaches will not, ordinarily, be suitable for treating cell-bearing liquids.

Cell-bearing liquids may be treated by mixing the particles in a container of the liquid or passing the liquid over a surface of the povidone-iodine material, e.g. over a multiple-plate array of sheets of such material. The povidone-iodine may be washed and the iodine content therein regenerated between uses.

In general a solution of reducing agent, e.g. a reducing sugar (or mixtures of reducing sugars), ascorbic acid or ascorbate, a sulfite, e.g. sodium sulfite, etc. in which the agent is in a concentration of 0.001 to 1 percent is suitable and such is implicit unless otherwise noted.

Similarly, PVP-I-PVP, and particularly PVP-I-PVPLMW, are preferred whenever povidone iodine is used.

Sperm cell containing compositions are manufactured using PVP-I-PVP, preferably PVP-I-PVPLMW, and a physiologically acceptable reducing agent or an suitable iodine absorbent, e.g. XLPVP. Such compositions can then be used safely for the induction of pregnancy in a female by inseminating the sperm cells into the female. The sperm cells are washed with povidone-iodine (PVP-I-PVP or PVP-I-PVPLMW) in water solution in a concentration of from $0.0^1$ to 10 weight percent, preferably from 0.1 to 5 w/o, sufficient to kill bacteria, viruses and other pathogenic micro-organisms but insufficient to inactivate the sperm cells. A reducing agent, e.g. an aqueous solution of from 0.001 to 1 percent reducing sugar (or mixtures of reducing sugars), ascorbic acid or ascorbate, a sulfite, e.g. sodium sulfite, etc., in an amount to reduce substantially all of the iodine. An aqueous PVP, especially PVPLMW (povidone in which the molecular weight is under about 12,000 daltons) may be used as the storage solution.

Transfusion or transplantation biological material from one human or mammal for transfusion or transplantation of such material to another human or mammal is manufactured using PVP-I-PVP, PVP-I-PVPLMW in particular, to treat the transplant or transfusion biological material to disinfected it. PVP-I-PVP or PVP-I-PVPLMW in which the povidone-iodine concentration is from $0.0^1$ to 10 weight percent, preferably from 0.1 to 5 w/o is suitable. Thereafter a solution of reducing agent, , e.g. a reducing sugar (or mixtures of reducing sugars), ascorbic acid or ascorbate, a sulfite, e.g. sodium sulfite, in a concentration of 0.001 to 1 percent being satisfactory, though higher concentrations could be used, is used to treat such material to reduce the residual iodine.

Blood derivatives are disinfected by treating blood before separation of the components thereof with povidone-iodine, e.g. PVP-I-PVP and preferably PVP-I-PVPLMW, to provide from a concentration of $0.0^1$ to 10 weight percent, preferably from 0.1 to 5 w/o povidone-iodine in the blood and then preparing a derivative of the blood. The derivative is then treated with povidone-iodine, PVP-I-PVP and preferably PVP-I-PVPLMW, to provide from $0.0^1$ to 10 weight percent, preferably from 0.1 to 5 w/o iodine in the derivative. Finally, the derivative by addition of a physiologically acceptable reducing agent, e.g. a 0.001 to 1 percent solution of, e.g. a reducing sugar (or mixtures of reducing sugars), ascorbic acid or ascorbate, a sulfite, e.g. sodium sulfite, or by contact with cross-linked PVP to reduce or remove residual iodine.

The invention is applicable to the manufacture of a drug delivery material comprising blood cell concentrate wherein the cell walls of the cells have been opened by treatment with from 0.01 w/o to 10 w/o povidone-iodine, PVP-I-PVP or PVP-I-PVPLMW, a drug has been introduced into the cells through passages produced by the povidone-iodine treatment, the cell walls have been sealed by heating the cells to from 42° to 48° C. and the resulting material having been treated by addition of a physiologically acceptable reducing agent, as described, or contact with cross-linked PVP to reduce or remove residual iodine.

Blood cells are treated by adding povidone-iodine, e.g. PVP-I-PVP and preferably PVP-I-PVPLMW, to the cell-containing milieu in a povidone iodine concentration of from $0.0^1$ to 10 weight percent, preferably from 0.1 to 1 w/o (100 to 1000 ppm $I_2$) sufficient to arrest or inhibit the principal metabolic functions of the blood cells but insufficient to kill the blood cells. The blood cells are stored for future use and thereafter treating the cells by addition of a physiologically acceptable reducing agent or contact with cross-linked PVP to reduce or remove residual iodine.

Packed red blood cells are treated to prevent the transmission of disease by mixing the red blood cells with povidone-iodine comprising at least ten percent povidone having a molecular weight of less than about 15,000 and having a povidone:iodine ratio of at least 15:1, said povidone-iodine being present in a concentration of from 0.001 to 0.1 weight percent. The red blood cells are allowed to remain in contact with the povidone-iodine compound for at least two minutes sufficient to inactivate or destroy infective pathogenic microorganisms and then treated by contact with cross-linked povidone or adding a physiologically acceptable reducing agent to remove oxidizing iodine and transfusing the thus treated red blood cells into a patient.

Blood is treated to prevent the transmission of disease by mixing the blood with povidone-iodine comprising at least ten percent povidone having a molecular weight of less than about 15,000 and having a povidone:iodine ratio of at least 15:1, said povidone-iodine being present in a concentration of from 0.001 to 0.1 weight percent. The blood is allowed to remain in contact with said povidone-iodine compound for at least two minutes sufficient to inactivate or destroy infective pathogenic microorganisms and thereafter contacted with cross-linked povidone or treated by adding a physiologically acceptable reducing agent to remove oxidizing iodine and transfusing the thus treated blood into a patient.

Nutrient for culture media is treated to prevent the transmission of disease by mixing said nutrient with povidone-iodine compound in a concentration of from 0.001 to 0.1 weight percent and allowing contact of said nutrient with said povidone-iodine compound for at least two minutes sufficient to inactivate or destroy infective pathogenic microorganisms. The media is contacted with cross-linked povidone or treated by adding a physiologically acceptable reducing agent to remove oxidizing iodine. Thereafter the nutrient is infused into a tissue culture medium.

Cell-bearing liquid is treated by contacting the liquid to be purified into contact with solid povidone-iodine, e.g. PVP-I-PVPXL or XLPVP-I, having sufficient surface area to introduce iodine into the liquid to sufficient to kill pathogenic organisms therein. The liquid is contacted with the solid povidone-iodine and treated by contact with cross-linked povidone or adding a physiologically acceptable reducing agent to remove oxidizing iodine.

Patients are treated with plasma by collecting plasma from a donor, and thereafter infusing the plasma into the patient to be treated. The plasma is mixed with povidone-iodine, e.g. PVP-I-PVP or PVP-I-PVPLMW, sufficient to resulting a povidone-iodine a concentration of from about $0.0^1$ to 10 weight percent, preferably from 0.1 to about 5 w/o, and allow to contact said povidone-iodine for at least about one-half minute sufficient to inactivate or destroy infective pathogenic microbes in the plasma. Thereafter, oxidizing iodine is removed from the resulting mixture by passing said mixture into intimate contact with cross-linked povidone or adding a physiologically acceptable reducing agent.

Plasma derivatives are disinfected by treating plasma before separation of the components thereof with povidone-iodine, e.g. PVP-I-PVP or PVP-I-PVPLMW, to provide from about $0.0^1$ to 10 weight percent, preferably from 0.1 to about 5 w/o, povidone-iodine in the plasma, then preparing a derivative of the plasma and thereafter treating the derivative with povidone-iodine, e.g. PVP-I-PVP or PVP-I-PVPLMW, to provide from about $0.0^1$ to 10 weight percent, preferably from 0.1 to about 5 w/o, povidone-iodine in the derivative and then removing oxidizing iodine from the derivative by passing said derivative into intimate contact with cross-linked povidone or adding a physiologically acceptable reducing agent, e.g., a reducing sugar (or mixtures of reducing sugars), ascorbic acid or ascorbate, a sulfite, e.g. sodium sulfite, etc.

Plasma factors are separated by alcohol fractionation with the addition of povidone-iodine to the plasma before fractionation in concentrations to provide from about 0.01 w/o to about 10 w/o, preferably from 0.1 to 5 weight percent, povidone-iodine in the plasma to give higher yields and sharper differentiation. Thereafter, oxidizing iodine is removed from the fraction by passing said fraction into intimate contact with cross-linked povidone or adding a physiologically acceptable reducing agent.

Patients are treated with plasma by collecting plasma from a donor, and thereafter infusing the plasma into the patient to be treated. The plasma is treated after collection and before infusion with povidone-iodine with added povidone to give a povidone to iodine ratio of at least about 15:1, preferably from about 20:1 to 30:1 and optionally up to about 60:1, sufficient to resulting an iodine a concentration of from about $0.0^1$ to 10 weight percent, preferably from 0.1 to about 5 w/o, and allowing contact of said plasma with said povidone-iodine with added povidone to give a povidone to iodine ratio of at least about 12 to 1 for at least about one-half minute sufficient to inactivate or destroy infective pathogenic microbes in the plasma. Thereafter oxidizing iodine is removed from the plasma by passing said plasma into intimate contact with cross-linked povidone or adding a physiologically acceptable reducing agent, , e.g. a reducing sugar (or mixtures of reducing sugars), ascorbic acid or ascorbate, a sulfite, e.g. sodium sulfite, etc..

Nutrient for culture media is treated to prevent the propagation of microbes in tissue culture media by mixing said nutrient with povidone-iodine with added povidone to give a povidone to iodine ratio of at least about 15 to 1 in a concentration to produce a povidone-iodine concentration of from about $0.0^1$ to 10 weight percent, preferably from 0.1 to about 5 w/o and allowing contact of said nutrient with said povidone-iodine for at least about one half minute sufficient to inactivate or destroy infective pathogenic microorganisms to thereby produce a nutrient which is free of both viable cells and viable microorganisms, and thereafter removing oxidizing iodine from the nutrient by passing said nutrient into intimate contact with cross-linked povidone or adding a physiologically acceptable reducing agent,, e.g. a reducing sugar (or mixtures of reducing sugars), ascorbic acid or ascorbate, a sulfite, e.g. sodium sulfite, etc.

A method of disinfecting plasma derivatives comprises the steps of treating plasma before separation of the components thereof with povidone-iodine with added povidone to give a povidone to povidone-iodine ratio of at least about 12 to 1 in an amount sufficient to provide from about $0.0^1$ to 10 weight percent, preferably from 0.1 to about 5 w/o, povidone-iodine in the plasma, preparing a derivative of the plasma, treating the derivative with povidone-iodine to provide from about $0.0^1$ to 10 weight percent, preferably from 0.1 to about 5 w/o, povidone-iodine in the derivative and thereafter removing oxidizing iodine from the plasma or a derivative thereof by passing said plasma or derivative into intimate contact with cross-linked povidone or adding a physiologically acceptable reducing agent, , e.g. a reducing sugar (or mixtures of reducing sugars), ascorbic acid or ascorbate, a sulfite, e.g. sodium sulfite, etc.

An improved method of separation of plasma factors by alcohol fractionation comprises the addition of povidone-iodine to the plasma before fractionation, the povidone-iodine with added povidone to give a povidone to iodine ratio in the plasma of at least about 15 to 1, in concentrations to provide from about 0.01 w/o to about 10 w/o povidone-iodine to give higher yields and sharper differentiation. Thereafter oxidizing iodine is removed from the factor by passing the plasma or factor thereof into intimate contact with cross-linked povidone or adding a physiologically acceptable reducing agent.

Platelet concentrates prepared by adding solid, e.g. cross-linked, povidone iodine, XLPVP-I, to a platelet-bearing liquid, separating the platelets from the XLPVP-I, by, e.g., soft spinning the XLPVP-I down in a centrifuge, and quenching the platelet concentrate by addition of a reducing agent results in platelets that a free of pathogens and retain their normal physiological characteristics. Other cell-bearing liquids may be treated in a similar manner.

An improved method of separation of plasma fractions by cryoprecipitation comprises the addition of povidone-iodine to the plasma before cryoprecipitation, the povidone-iodine with added povidone to give a povidone to iodine ratio in the plasma of at least about 15 to 1, in concentrations to provide from about $0.0^1$ to 10 weight percent, preferably from 0.1 to about 5 w/o, povidone-iodine to give higher yields and sharper differentiation and thereafter removing oxidizing iodine from the cryoprecipitate or a fraction thereof by passing said cryoprecipitate or fraction thereof into intimate contact with cross-linked povidone or adding a physiologically acceptable reducing agent.

An apparatus for treatment of liquid to kill microbes therein comprises a liquid container having, in use an upper reservoir portion for holding said liquid and a lower elutriation portion for recovering liquid and structure defining first and second beds of particulate matter, the first bed comprising substantially insoluble povidone iodine and the second bed consisting essentially of substantially insoluble povidone. The beds are so formed and configured as to permit the passage of the liquid therethrough in intimate contact with the surfaces of the particles forming the respective beds. The substantially insoluble povidone is preferably cross-linked povidone, XLPVP.

An additional layer may be provided between the first and second layers comprising substantially insoluble povidone hydrogen peroxide particulate matter. Still another layer of particulate matter below the second layer comprising an iodine reducing agent may also be provided. Yet another additional layer may be provided, such layer being formed of soluble povidone iodine disposed on the first layer in the liquid reservoir. This may be soluble povidone on the top of the first layer for being dissolved into the liquid to be treated. The soluble povidone may comprises at least about one-fourth polyvinylpyrrolidone having a molecular weight not higher than about 15,000.

The apparatus may also comprise soluble povidone-hydrogen peroxide on the top of the first layer for being dissolved into the liquid to be treated.

The insoluble povidone iodine particles of the first layer are physically supported by a layer of fibrous material or povidone attached to carrier particles, e.g. activated charcoal particles. The particulate matter preferably consists essentially of particles having a diameter of from about 10 to about 100 microns.

A method of treating biological liquids to kill microbes comprises the steps of introducing oxidizing iodine into the liquid to be treated, allowing the oxidizing iodine to remain in contact and at least partially in solution in said liquid for a period of at least about one-half minute but not more than about one hour, optionally followed by quenching the oxidizing iodine in said liquid to remove or reduce substantially oxidizing iodine by causing (i) the liquid intimately to contact cross-linked povidone iodine, or (ii) introducing an iodine reducing agent into said liquid, or (iii) both (i) and (ii). In addition, povidone-hydrogen peroxide may be introduced into said liquid. Soluble povidone is preferably added to the liquid to be treated before adding the oxidizing iodine. Preferably, more than half of the povidone iodine added before adding the oxidizing iodine is low molecular weight povidone iodine having an average molecular weight below about 15,0000.

A method of sterilizing an implantable tissue comprises placing tissue that is physiologically acceptable for implantation into a human patient into a vacuum chamber, evacuating said chamber and maintaining a vacuum on said chamber for a period long enough to extract at least about one-half of the unbound water originally present in said tissue, and introducing into said vacuum chamber a solution of povidone iodine, e.g. PVP-I-PVP or, preferably, PVP-I-PVPLMW, for thereby reconstituting into the tissue said solution in place of the water that was vacuum extracted. Further, the thus treated tissue may be soaked in a solution of an physiologically acceptable iodine reducing agent to assure total removal of oxidizing iodine. Or, the chamber may be evacuated to extract the povidone iodine solution and a solution of physiologically acceptable iodine reducing agent introduced into the vacuum chamber for saturating the tissue with said solution for reducing any residual iodine.

Industrial Application

This invention finds application in medicine and veterinary science.

What is claimed is:

1. An apparatus for treatment of liquid to kill microbes therein comprising a liquid container having, in use an upper reservoir portion for holding said liquid and a lower elutriation portion for recovering liquid and structure defining first and second beds of particulate matter, the first bed comprising substantially insoluble povidone iodine and the second bed consisting essentially of substantially insoluble povidone; the beds being so formed and configured as to permit the passage of the liquid therethrough in intimate contact with the surfaces of the particles forming the respective beds.

2. The apparatus of claim 1 further comprising an additional layer between the first and second layers, said additional layer comprising substantially insoluble povidone hydrogen peroxide particulate matter.

3. The apparatus of claim 1 further comprising an additional layer of particulate matter below the second layer comprising an iodine reducing agent.

4. The apparatus of claim 1 further comprising a layer of soluble povidone iodine on the first layer in the liquid reservoir.

5. The apparatus of claim 1 wherein the soluble povidone comprises at least about one-fourth polyvinylpyrrolidone having a molecular weight not higher than about 15,000.

6. The apparatus of claim 1 further comprising soluble povidone-hydrogen peroxide on the top of the first layer for being dissolved into the liquid to be treated.

7. The apparatus of claim 1 wherein the particulate matter consists essentially of particles having a diameter of from about 10 to about 100 microns.

* * * * *